United States Defensive Publication [19] (H) [11] T102,907

Halfon et al. [43] Apr. 5, 1983

[54] PROCESS TO 3-PHENOXYBENZYL 3-(2,2-DICHLOROVINYL)-2,2-DIMETHYL-CYCLOPROPANECARBOXYLATE

[76] Inventors: Marc Halfon, P.O. Box 64, 10-14 Deer Creek Dr., Plainsboro, N.J. 08536; William G. Scharpf, 804 Roelofs Rd., Yardley, Pa. 19067

[21] Appl. No.: 381,997

[22] Filed: May 25, 1982

Related U.S. Application Data

[63] Continuation of Ser. No. 10,183, Feb. 7, 1979, abandoned.

[51] Int. Cl.[3] ..... C07C 69/743

[52] U.S. Cl. ..... 560/124

[57] ABSTRACT

3-Phenoxybenzyl 3-(2,2-dichlorovinyl)-2,2-dimethylcyclopropanecarboxylate is prepared in greater than 90% yield by alcoholysis of lower alkyl 3-(2,2-dichlorovinyl)-2,2-dimethylcyclopropanecarboxylates with 3-phenoxybenzyl alcohol. A lower alkyl alcohol, e.g., methanol or ethanol, is generated as a by-product.

The process is conducted under reflux at a temperature of at least 100° C. in an inert solvent between approximately stoichiometric amounts of the reactants. The solvent is selected to form an azeotropic mixture with, or boil at a higher temperature than, the lower alkyl alcohol by-product, and the by-product is removed from the mixture by distillation as it is produced. If lower alkyl is methyl or ethyl, n-octane, benzene, toluene, xylene, or mesitylene may be employed, for example.

The process is promoted by lower alkyl titanium alkoxide catalysts. The purity of the product 3-phenoxybenzyl 3-(2,2-dichlorovinyl)-2,2-dimethylcyclopropanecarboxylate, which is obtained as a bottoms residue after stripping the solvent, is high enough, greater than 90%, to be suitable for use in commerce as the pyrethroid insecticide "permethrin" without further purification. The purity is enhanced by the use of only 0.001–0.01 mole of the catalyst per mole of lower alkyl 3-(2,2-dichlorovinyl)-2,2-dimethylcyclopropanecarboxylate. To avoid hydrolysis of the catalyst, the reaction is carried out under substantially anhydrous conditions.

1 Claim, No Sheets Drawing,

10 Pages Specification

The file of this unexamined application may be inspected and copies thereof may be purchased (849 O.G. 1221, Apr. 9, 1968).